United States Patent [19]
Pozniak et al.

[11] Patent Number: 6,099,516
[45] Date of Patent: *Aug. 8, 2000

[54] FASTENER SYSTEM FOR USE WITH PERSONAL CARE ARTICLES

[75] Inventors: Jennifer Elizabeth Pozniak, Appleton; Thomas Harold Roessler, Menasha; John Philip Vukos, Neenah; Georgia Lynn Zehner, Larsen, all of Wis.

[73] Assignee: Kimberly-Clark Worldwide, Inc., Neenah, Wis.

[ * ] Notice: This patent issued on a continued prosecution application filed under 37 CFR 1.53(d), and is subject to the twenty year patent term provisions of 35 U.S.C. 154(a)(2).

[21] Appl. No.: 08/960,804

[22] Filed: Oct. 30, 1997

[51] Int. Cl.$^7$ ...................................................... A61F 13/15
[52] U.S. Cl. ............................ 604/386; 604/391; 24/304; 2/300; 2/400
[58] Field of Search ...................................... 604/386, 389, 604/390, 391; 24/450, 451, 304; 2/300, 400, 914, 919

[56] References Cited

U.S. PATENT DOCUMENTS

| | | | |
|---|---|---|---|
| 4,617,022 | 10/1986 | Pigneul et al. | 604/391 |
| 4,699,622 | 10/1987 | Toussant et al. | 604/389 |
| 4,704,116 | 11/1987 | Enloc . | |
| 4,936,840 | 6/1990 | Proxmira | 604/391 |
| 5,226,992 | 7/1993 | Morman | 156/62.4 |
| 5,288,546 | 2/1994 | Roessler et al. | 428/284 |
| 5,516,567 | 5/1996 | Roessler et al. | 428/40.1 |
| 5,554,143 | 9/1996 | Roe et al. | 604/385.2 |
| 5,593,401 | 1/1997 | Sosalla et al. | 604/385.2 |
| 5,605,735 | 2/1997 | Zehner et al. | 428/100 |
| 5,624,429 | 4/1997 | Long et al. | 604/391 |
| 5,722,127 | 3/1998 | Coates | 24/450 |
| 5,769,832 | 6/1998 | Hasse | 604/391 |
| 5,782,819 | 7/1998 | Tanzer et al. | 604/385.1 |

FOREIGN PATENT DOCUMENTS

| | | | |
|---|---|---|---|
| 487758 | 6/1992 | European Pat. Off. | 604/386 |
| 704196 | 3/1996 | European Pat. Off. | 604/386 |
| 1253704 | 1/1961 | France | 24/450 |

*Primary Examiner*—Mark O. Polutta
*Attorney, Agent, or Firm*—Michael L. Winkelman; Thomas D. Wilhelm

[57] ABSTRACT

A fastener system for use with personal care articles includes a substrate formed by a bodyside linear and an outer cover. Fastening tabs are secured to the substrate at opposing sides of the rear portion of the article. The fastening tabs include friction zones that, when the tabs are mounted to the article, provide substantially no securement to the article, and securing zones that secure the respective fastening tabs to the outer cover at a front portion of the article. The friction zones prevent surface-to-surface radial shifting or bending of the front portion with respect to the fastening tabs of the article during regular usage. In one embodiment, a tab substrate provides a mounting surface for a friction element and a securing element which form the respective friction zone and securing zone. In another embodiment, the friction element functions as a substrate supporting the securing element. The friction element resists relative movement of the front portion of the article with respect to the rear portion and thus stabilizes the article on the wearer.

52 Claims, 5 Drawing Sheets

FASTENER SYSTEM FOR USE WITH PERSONAL CARE ARTICLES

CROSS REFERENCE TO RELATED APPLICATIONS

Not Applicable

STATEMENT REGARDING FEDERALLY SPONSORED RESEARCH OR DEVELOPMENT

Not Applicable

FIELD OF THE INVENTION

Personal care articles such as infant diapers, training pants, adult incontinence products, and the like are well known. Such personal care articles have achieved wide acceptance due to their ability to receive and absorb body exudates, whether large amounts or small, and may or may not include an absorbent core or pad therein.

This invention pertains to fastener systems for such articles. Such fastener systems include fastening tabs having securing zones and friction zones. The fastener system secures the personal care article to the body of a user. In one embodiment, a pair of fastening tabs extend outwardly from opposing sides of a rear portion of the personal care article for selective securement to the front portion of the article.

BACKGROUND OF THE INVENTION

In general, personal care articles should comfortably fit the body of a wearer. However, personal care articles must also contain the designed quantity of body exudates and thus must fit properly. Personal care articles generally have tabs at the rear of the personal care article that extend outwardly and secure to a front portion of the article. Such tabs may employ flexible microhook fasteners. When securely fastened to the body of a wearer, some known fastening tabs may be positioned relative tightly against the body of the user. During normal wear, including normal movements of the wearer, microhooks on the tab may contact the skin of the wearer and may respectively irritate the skin of the wearer. This occurs in large part at the edges of the fastening tab, as the tab becomes exposed to the skin when the front panel and rear panel of the personal care article do not entirely cover the skin, or as the user lifts up a leg, moving the panels of the personal care article apart, whereby the skin of the wearer contacts the microhooks. The closer the microhooks are positioned to the side edges of the personal care article, the more likely that the microhooks will contact the user's skin, thus effecting the above described irritation. Thus, some hooks of secured fastening tabs cause red marks on the skin of a wearer. The invention overcomes this problem and improves the relative comfort and securement of the personal care article relative to the body of a user.

SUMMARY OF THE DISCLOSURE

In the present invention, fastening tabs for securing the rear portion to the front portion of a personal care article include a friction zone for preventing radial shifting of the front portion with respect to the fastening tab during normal usage. The friction zone is formed by a friction element having sufficient softness to provide comfort when contacting the skin of a wearer.

In one embodiment, the fastening tab has first and second sides, a length, and a width, the first side of the fastening tab comprising a first surface, a securing zone for securing the fastening tab, as part of a personal care article, to an outer cover, and a friction zone, the first surface at the friction zone having substantially no securement properties, and having a kinetic coefficient of friction of at least about 1.5 when measured against a polypropylene necked spunbond laminate, the spunbond laminate comprising first and second polypropylene spunbond layers having a weight of about 0.65 to about 0.70 ounces per square yard after necking, and a fiber size of about 2 to about 2.5 denier, the necked spunbond laminate including an elastomeric film core in surface-to-surface relationship with the spunbond layers, the coefficient of friction measured at a temperature of between about 22 degrees and about 24 degrees Celsius, when the friction zone is secured to a 100 gram sled and the polypropylene necked spunbond laminate is secured to a moving platen, the coefficient of friction between the friction zone and the outer cover being sufficient to prevent surface-to-surface radial shifting of the front portion with respect to the fastening tab during normal usage.

In most embodiments the fastening tab includes a tab substrate disposed toward the second side of the fastening tab and thus underlying the securing zone and the friction zone. The tab substrate preferably comprises a nonwoven material.

In most embodiments the securing zone comprises a securing element mounted in surface-to-surface relationship to the tab substrate at the securing zone. The securing element preferably comprises hooks or microhooks. However, the securing element can comprise loops of a hook and loop fastener system for releasably securing the tab to the front portion of a personal care article. The securing element can be permanently secured to the tab substrate by adhesive.

In most embodiments, the friction zone comprises a friction element, mounted in surface-to-surface relationship to a friction surface area, corresponding to the friction zone, on the first side of the tab substrate. The friction element preferably comprises a foam material, such as an open-cell flexible polyurethane foam. The foam material has an uncompressed thickness of less than about 10 millimeters, preferably less than about 5 millimeters, and most preferably less than about two millimeters.

In another embodiment, the friction element extends substantially the entire length and width of the fastening tab. Thus the friction element also functions as the tab substrate. The securing zone comprises a securing element attached in surface-to-surface relationship with a portion of a first surface of the friction element. The friction element is secured to a personal care article thus forming a fastening tab.

The friction zone preferably is free from functional amounts of tackifying agents. Thus the friction zone provides friction against relative movement of the front portion of the personal care article relative to the fastening tab.

In some embodiments, especially those having a nonextensible outer cover and a nonextensible bodyside liner, the fastening tab can be extensible.

Another family of embodiments include a personal care article having a front portion, a rear portion, and a crotch portion, the personal article comprising a body substrate, including an outer cover, and a bodyside liner in facing relation with the outer cover, and first and second fastening tabs, secured to and extending outwardly from the substrate at opposing sides of the rear portion of the personal use article. The fastening tabs includes securing zones located proximate outboard ends of the tabs and friction zones located inwardly of the securing zones, the friction zones providing no securement of the tabs to the personal care article. The securing zones of the fastening tabs secure the tabs to the outer cover at the front portion of the personal care article and the friction zones stabilize the front portion with respect to the rear portion by resisting relative surface-to-surface movement of the front portion of the outer cover with respect to the fastening tabs.

In some embodiments, the personal care article includes an absorbent body located between the bodyside liner and the outer cover, the personal care article thus comprising an absorbent article for receiving exudates.

In some embodiments, the friction elements comprise foam materials having sufficient softness to avoid red marking of a leg of a wearer at leg openings closed by respective fastening tabs.

In some embodiments, the friction zone extend inwardly on the respective fastening tabs such that the friction zones extend over part of the substrate at opposing sides of the rear portion of the article.

In some embodiments, the outer cover comprises a material having an extensibility in at least one direction. The bodyside liner comprises a material having an extensibility in at least one direction.

In some embodiments, the first and second fastening tabs are secured to the bodyside liner at opposing sides of the rear portion of the personal care article by ultrasonic bonding.

In some embodiments, the friction elements define friction zones at opposing sides of the front portion of the personal use article, the friction elements being permanently secured to the outer cover at the opposing sides. The friction elements provide no securement of the front portion to the fastening tabs or rear portion, the securing zones of the fastening tabs securing the tabs to the outer cover at the front portion of the personal care article. The securing zones are placed inwardly from the friction elements when secured to the body of a wearer. The friction elements stabilize the front portion with respect to the rear portion by contacting the respective fastening tabs or the rear portion of the personal use article, and resist relative surface-to-surface movement of the fastening tabs with respect to the front portion.

In other embodiments of the invention, the personal care article has a body substrate, including an outer cover, and a bodyside liner, and first and second fastening tabs at opposing sides of the rear portion of the personal use article, the fastening tabs including friction zones comprising friction elements, the friction elements providing substantially no securement of the fastening tabs to the personal care article, the friction elements having a kinetic coefficient of friction of at least about 1.5 when measured against the outer cover.

Figure 1:
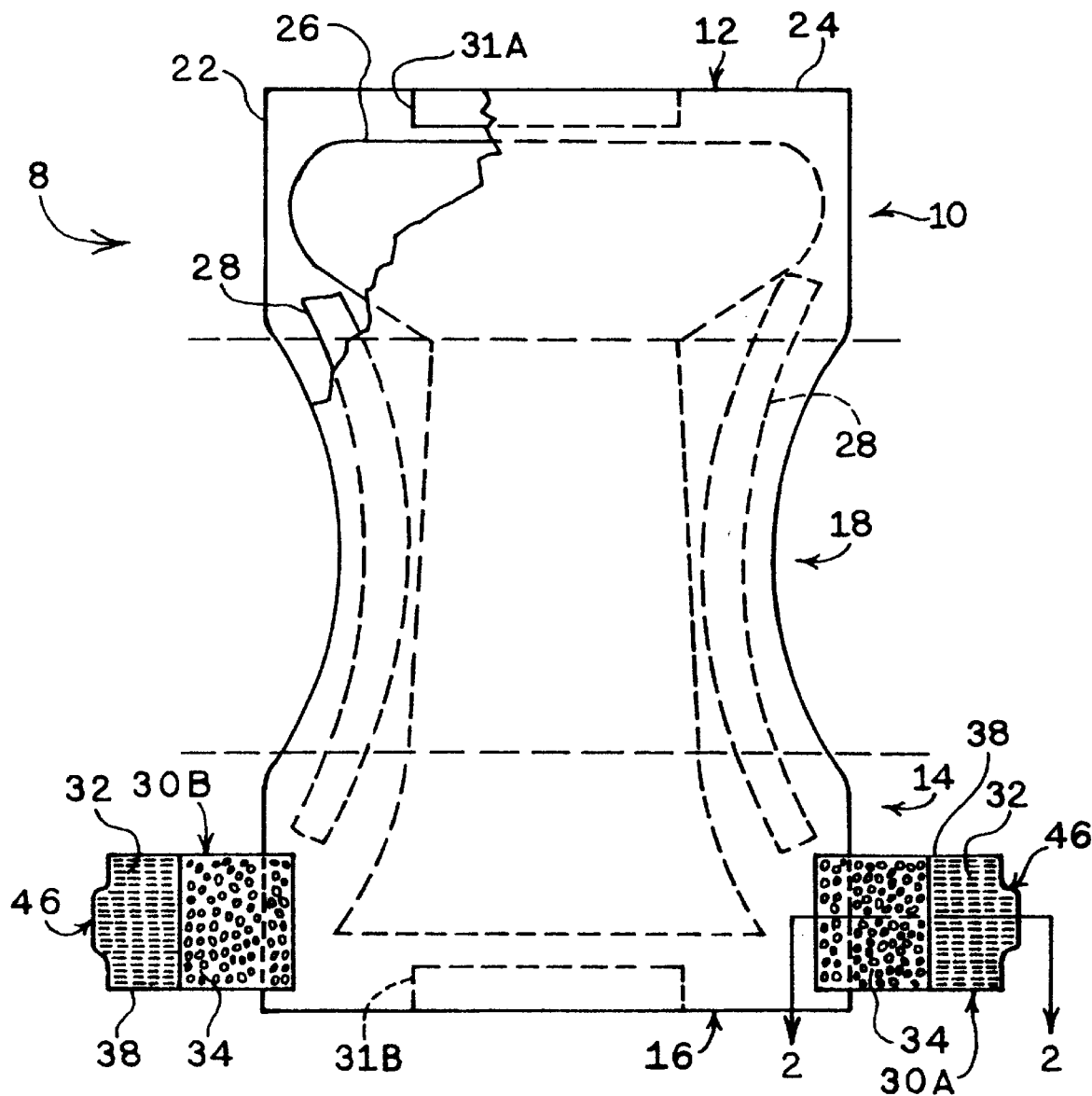
FIG. 1 shows a top view of a first embodiment of personal care articles of the invention.

The invention is not limited in its application to the details of the construction and the arrangement of the components set forth in the following description or illustrated in the drawings. The invention is capable of other embodiments or of being practiced or carried out in various ways. Also, it is to be understood that the terminology and phraseology employed herein is for purpose of description and illustration and should not be regarded as limiting. Like reference numerals are used to indicate like components. The drawings are for purposes of illustration, and are not necessarily drawn to scale.

DETAILED DESCRIPTION OF THE ILLUSTRATED EMBODIMENTS

The various embodiments of the present invention will be described in relationship to their use in disposable personal care articles, but it should be understood that potential uses of the structures of the present invention need not be limited to the context of disposable personal care articles. Other uses for the present invention include other articles, such as caps, gowns, shoe covers, feminine care articles, incontinence garments or the like.

As used herein and in the claims that follow, the phrase "personal care article" is meant to include diapers, training pants, adult incontinence articles, feminine hygiene products, and the like. Such articles may have no significant absorbent function, but may receive and/or store urine and/or fecal material, or may have a significant absorbent function, and may receive and/or store urine and/or fecal material.

Figure 2:
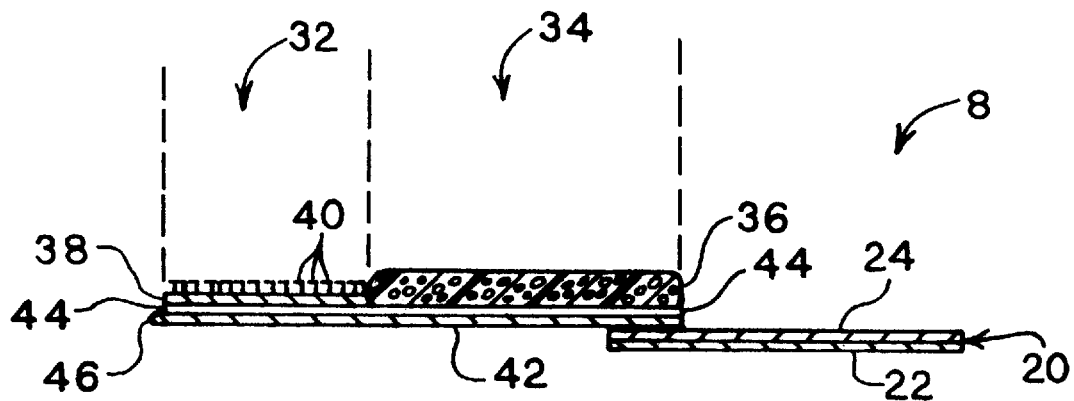
FIG. 2 shows a cross section of a first tab of the personal care articles of FIG. 1.

Personal care article 8, shown in FIGS. 1 and 2, includes a front portion 10 having a front edge 12, a rear portion 14 having a rear edge 16, and a crotch portion 18 between front portion 10 and rear portion 14. Personal care article 8 includes a body substrate 20 formed, in combination, by an outer cover 22 and a bodyside liner 24. Absorbent body 26 preferably is located between bodyside liner 24 and outer cover 22. Absorbent body 26 receives and retains exudates which pass through bodyside liner 24. Leg cuffs 28 provide support in the crotch portion.

FIG. 1 is a representative plan view of personal care article 8 in its uncontracted state (i.e. with all elastic induced gathering and contraction removed). The top left corner of article 8 is cut away to better show outer cover 22 and absorbent body 26. Fastening tabs 30A, 30B are secured to bodyside liner 24 by ultrasonic bonding at opposing sides of rear portion 14 of personal care article 8. Fastening tabs 30A, 30B extend outwardly from the sides of rear portion 14. Waist elastics 31A, 31B are located near front edge 12 and rear edge 16, respectively, of personal care article 8.

Each fastening tab 30A, 30B includes a securing zone 32 and a friction zone 34. In use on a wearer, securing zone 32 is used to secure fastening tab 30A to front portion 10 of personal care article 8, thereby to maintain the article suitably mounted on the wearer. Securing zone 32 is located proximate the distal edge of the respective tab, thus outward of friction zone 34. Securing element 32 need not extend to the distal edge of the substrate. At least a portion of the distal edge may be used as a grip tab portion (not shown) permitting a user to comfortably grasp and locate fastening tab 30A at a proper mounting position.

Figure 3:
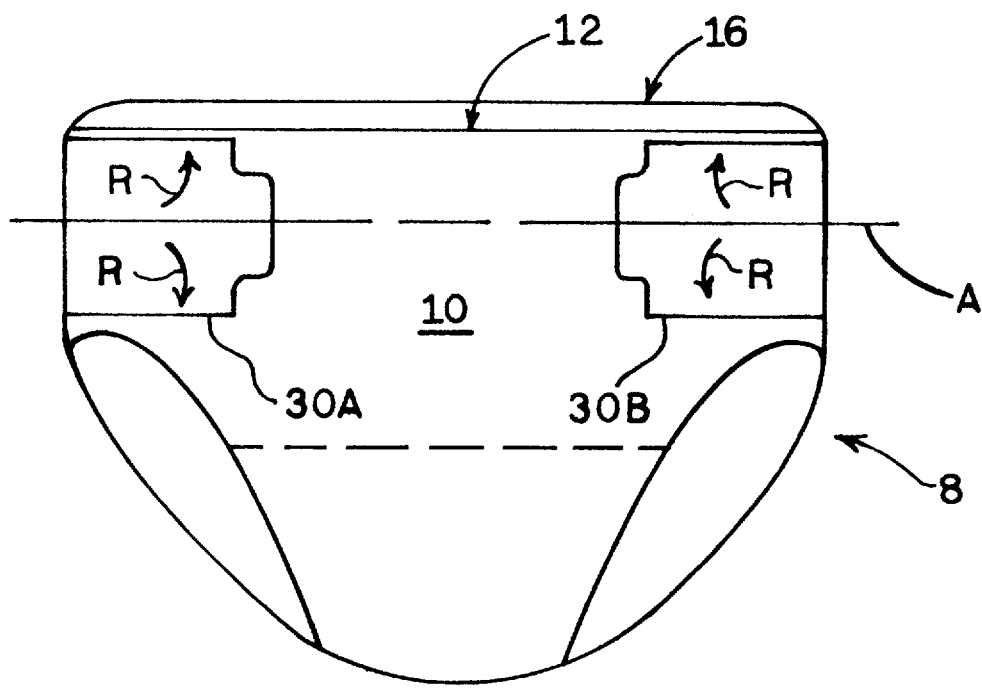
FIG. 3 shows the first embodiment having fastening tabs secured to the front portion of the personal care article.

Friction zone 34 provides friction between the outer surface of the friction zone and the outer mounting surface e.g. at outer cover 22 on front portion 10 of body substrate 20 such that relative surface-to-surface movement between fastening tab 30A and the body substrate is resisted. Thus, as shown in FIG. 3, when friction zone 34 contacts over cover 22 in surface-to-surface relationship, the high coefficient of friction strongly inhibits relative movement of fastening tab 30A with respect to outer cover 22. Thus friction zone 34 prevents radial shifting or twisting of fastening tabs 30A, 30B relative to outer cover 2 about axis "A" in response to body forces of a user wearing personal care article 8. Rather, friction zone 34 assists in inhibiting radial shifting of, or relative surface-to-surface movement of front portion 10 with respect to fastening tabs 30A, 30B during normal movements of the wearer. Arrows "R" in FIG. 3 illustrate the various directions front portion 10 may want to shift or rotate, relative to fastening tabs 30A, 30B. Likewise, front portion 10 of personal care article 8, under certain conditions, may want to shift in the directions shown by arrows "R" relative to fastening tabs 30A, 30B. In this manner, friction zone 34 indirectly assists securing zone 32 in resisting release of fastening tab 30A due to forces transferred from front portion 10 of personal care article 8, through the fastening tabs, and through rear portion 14. However, friction zone 34 has no securement properties defining adhesive-type tack between fastening tab 30A and outer cover 22. Thus friction zone 34 does not provide any securement in attaching fastening tab 30A to front portion 10 of body substrate 20.

In other less preferred embodiments, Axis "A" can comprise two axes (not shown) not parallel to front edge 12 of personal care article 8. Thus the axes can be at oblique angles with respect to front edge 12 of personal care article 8.

As representatively shown, bodyside liner 24 and outer cover 22 may be generally coextensive and may have length and width dimensions which are generally larger than the dimensions of absorbent body 26. Bodyside liner 24 is associated with and generally superimposed over the entirety of the surface of outer cover 22, thereby defining the periphery of personal care article 8. Absorbent body 26 is optionally disposed between outer cover 22 and bodyside liner 24 inboard of the periphery of the article 8.

Outer cover 22 preferably comprises a material which is configured to be substantially impermeable to liquids. For example, a typical outer cover 22 can be manufactured from a thin plastic film or other flexible liquid-impermeable material.

In some embodiments, outer cover 22 is a polyethylene film having a thickness of from about 0.012 millimeters to about 0.051 millimeters. Alternative constructions of outer cover 22 may comprise a woven or non-woven fibrous web layer which has been totally or partially constructed or treated to impart the desired levels of liquid impermeability to selected regions thereof, such as regions that are adjacent or proximate absorbent body 26. Optionally, in some embodiments, an additional outer cover may overlay outer cover 22.

Outer cover 22 may optionally be composed of microporous, breathable material that permits vapors to escape from the absorbent article while preventing liquid exudates from passing through. For example, a suitable microporous film is a material known as PMP-1, which is available from Mitsui Toatsu Chemicals, Inc. a company having offices in Tokyo, Japan; or polyolefin film known as XKO-8044 and available from 3M Company of Minneapolis, Minn.

In another embodiment of the invention, outer cover 22 can be a nonwoven, spunbond polypropylene fabric. The fabric can be creped or necked such that it is extensible in at least one of the "x" and "y" directions or in both the machine direction and the cross direction. Other materials having other advantageous characteristics are also useful as outer cove 22. For example, outer cover 22 can comprise a stretch-bonded laminate. Methods of making such materials are known to those skilled in the art.

Bodyside liner 24 includes a skin-facing surface which is compliant, soft-feeling, and non-irritating to the wearer's skin. Further, bodyside liner 24 can be sufficiently porous to be liquid permeable, permitting liquid to penetrate through its thickness.

A suitable bodyside liner 24 may be manufactured from a wide selection of web materials, such as porous foams, reticulated foams, apertured plastic films, woven and/or nonwoven natural fibers, synthetic fibers, or a combination of natural and synthetic fibers. Bodyside linear 24 is typically employed to help isolate the wearer's skin from liquids held in absorbent body 26. Various woven and nonwoven fabrics can be used for bodyside liner 24. For example, bodyside liner 24 may be composed of a meltblown or spunbonded web of polyolefin fibers. Bodyside liner 24 may also be a bonded-carded-web composed of natural and/or synthetic fibers.

Bodyside liner 24 may be composed of a substantially hydrophobic and substantially nonwettable material, with the hydrophobic material optionally being treated with a surfactant or otherwise processed to impart a desired level of wettability and hydrophilicity.

In another embodiment of the invention, bodyside liner 24 can be a nonwoven, spunbonded polypropylene fabric. The fabric can be creped or necked such that it is extensible in at least one of, or both of, the "x" and "y" directions (in the machine direction and/or the cross direction).

Bodyside liner 24 may comprise a multiplicity of components, layers, or partial layers, which correspond to any of the materials disclosed herein, as well as others known in the art. The fabric can be treated with a selected amount of surfactant, such as about 0.28% Trition X-102 surfactant available from Rohm and Haas Corp. of Philadelphia, Pa. The surfactant can be applied by any conventional means such as spraying, printing, brush coating or the like.

In yet another embodiment of the present invention, bodyside liner 24 can comprise a stretch-bonded laminate having appropriate elasticity and width to create overall surface contact between personal care article 8 and the body of a user. A stretch-bonded laminate comprises at least a two-layered composite in which one layer is a gatherable layer and the other layer a stretchable layer. The layers are joined together when the stretchable layer is in a stretched condition so that, upon relaxing the composite of the joined layers, the gatherable layer is gathered. The stretchable layer can be a film of stretchable material, such as a layer of styrene ethylene butylene styrene or other elastomeric polymer, or a plurality of strands of a stretchable material such as latex. Other materials with similar properties may also be provided integral with or attached to bodyside liner 24. Such materials should not interfere with the soft texture of bodyside liner 24 against the skin of a user.

Absorbent body 26 may be manufactured in a wide variety of sizes and shapes (for example, rectangular, trapezoidal, T-shape, I-shape, hourglass shape, etc.) and from a wide variety of materials. The size, and absorbent capacity, of absorbent body 26 should be compatible with the size of the intended wearer and the anticipated liquid loading imparted by the intended use of the absorbent body.

Absorbent body 26 suitably comprises a matrix of hydrophilic fibers, such as a web of cellulosic fluff, preferably in combination with a high-absorbency material commonly known as superabsorbent material. In a preferred embodiment, absorbent body 26 comprises a mixture of superabsorbent hydrogel-forming material and wood pulp fluff. In place of the wood pulp fluff, one may use synthetic, polymeric, meltblown fibers or a combination of meltblown fibers and natural fibers. The superabsorbent material may be substantially homogeneously mixed with the hydrophilic fibers or may be otherwise combined into the absorbent core.

Alternatively, absorbent body 26 may comprise a laminate of fibrous webs and superabsorbent material or other suitable means of maintaining a superabsorbent material in a localized area.

The high-absorbency material in absorbent body 26 can be selected from natural, synthetic and modified natural polymers and materials. The high absorbency materials can be inorganic materials, such as silica gels, or organic compounds, such as cross-linked polymers. The term cross-linked refers to any means for effectively rendering normally water-soluble materials substantially water insoluble but swellable, whereby absorbent properties are available but the swelled material is substantially immobile after absorbing water-based liquids. Such means can include, for example, physical entanglement, crystalline domains, covalent bonds, ionic complexes and associations, hydrophilic associations such as hydrogen bonding, and hydrophobic associations or Van der Waals forces.

Leg cuffs 28 may be formed from separate materials, preferably leg elastics, which are attached to outer cover 22 and/or bodyside liner 24. Materials suitable for forming the leg elastics include LYCRA® strands, ribbons, or one or more layers of a polymeric and/or elastomeric material which may be adhered in personal care article 8 forming leg cuff 28 while in a stretched position. Alternatively, the material can be attached, in a relaxed condition, to personal care article 8 while the article is pleated, such that elastic constrictive forces are imparted to leg cuff 28 when the leg cuff is elongated along the length of article 8.

In some embodiments where outer cover 22 and/or bodyside liner 24 are formed from stretchable materials, extensible leg cuffs need not be included in personal care article 8.

Waist elastics 31A, 31B generally extend about the waist of personal care article 8. Front waist elastics 31A and rear waist elastics 31B generally comprise strands, ribbons or one or more layers of a polymeric and/or elastomeric material which can be adhered in personal care article 8 while in a stretched condition. Front waist elastics 31A and rear waist elastics 31B can comprise one or more individual strands of elastomeric material, preferably in a spatially separated, generally parallel arrangement.

Waist elastics 31A, 31B preferably are adhesively secured to one of bodyside liner 24, or outer cover 22, and disposed between the bodyside liner and the outer cover. In the alternative, waist elastics 31A, 31B can be secured to both outer cover 22 and bodyside liner 24. In other embodiments, waist elastics 31A, 31B can be secured to the outwardly facing side of outer cover 22 or the body facing side of bodyside liner 24. The placement of waist elastic 31A, 31B with respect to the layer or layers forming body substrate 20 is not critical. However, waist elastics 31A, 31B should be located close to the respective edges 12, 16.

In embodiments comprising stretchable outer covers 22 and/or stretchable bodyside liners 24, waist elastics 31A, 31B can be omitted. Thus, in some embodiments, stretchable body substrate 20 obviates the need for waist elastics 31A, 31B while retaining the respective stretch function.

In some embodiments, opposing left and right spaced containment flaps (not shown) can extend longitudinally along the length of personal care article 8 inwardly of respective side edges of the personal care article. In such embodiments, the containment flaps are typically secured to bodyside liner 24. Some examples of containment flaps are set forth in U.S. Pat. No. 4,704,116 issued Nov. 3, 1987 to K. Enloe, the disclosure of which is hereby incorporated by reference in a manner that is consistent (not contradictory) herewith.

Containment flaps may, for example, be constructed of a fibrous material which is similar to the material comprising outer cover 22 or bodyside liner 24. Other suitable conventional materials, such as polymer films, may also be employed.

As better illustrated in FIG. 2, friction zone 34 is formed by a friction element 36 having a high coefficient of friction against front portion 10. Friction element 36 can comprise a foam material or other soft material having a high coefficient of friction. One example of friction element 36 is an open-cell flexible polyurethane foam. The foam material has sufficient softness that, when contacting the skin of a wearer, the material does not red-mark the skin during normal usage. Such materials also have a coefficient of friction large enough to resist surface-to-surface movement of fastening tab 30 against front portion 10 of personal care article 8.

Other materials having similar properties and a high coefficient of friction can also be utilized. For example, a meltblown nonwoven with fiber sizes less than 10 micrometers, having a basis weight of from 10 grams per square meter to 100 grams per square meter, formed from elastomeric polyethylene, such as Affinity 52800.02, manufactured by Dow Chemical Co. of Midland, Mich., may also be utilized for friction element 36.

Friction element 36 can also comprise films or coatings. For example, friction element 36 can comprise a coextruded film with a thickness of about 0.75 mils. The coextruded film may be composed of about 75% by weight layer of polyethylene and about 25% by weight layer of polyolefin. A suitable coextruded film is identified by the identification number XC2-21-826.1 and is available from Consolidated Thermoplastics Company of Chippewa Falls, Wis.

A skid resistant coating can form friction element 36. Such a coating can be formed from the following groups of materials: ethylene vinyl acetate copolymers applied as a hot melt or as a water based coating having at least 28% vinyl acetate; polyvinyl acetate in water-based emulsions; styrene-butadiene in an emulsion or as a hot melt; cellulose acetate butyrate in a hot melt; ethyl cellulose blended with a plasticizer and a resin; acrylics in an emulsion system that are not blended; synthetic rubber (KRATON® block copolymers having elastomeric and styrenic blocks), rubber, resin, plasticizer blends and hot melts including polyethylene (alone or blended) and polyamides among others.

Another embodiment of friction element 36 can comprise bristles (not shown), that are similar to the hook components 40 of a hook and loop fastener system. However, the bristles simply point straight, similar to a brush without a hook, mushroom, or other shape, that would snag front portion 10. Thus bristles result in substantially no securement. In this manner, the bristles provide shear strength to prevent radial shifting of fastening tab 30A with no significant securement to front portion 10.

Key features in the above compositions are having sufficient softness when contacting the skin of a wearer, and a high coefficient of friction to prevent radial shifting of front portion 10 of personal care article 8 with respect to fastening tabs 30A, 30B. Thus relative movement of front portion 10 with respect to rear portion 14 is minimized. By eliminating or reducing radial shifting of front portion 10 with respect to rear portion 14, sagging or drooping of personal care article 8 is decreased and performance of the article is enhanced.

TEST PROCEDURE

The following tests were performed to determine the coefficient of friction between two materials. The procedure determines the sustained sliding (kinetic) friction of a material when sliding over another material.

A sled, which has the test specimen attached thereto, is pulled over a moving platen (table) that has another testing material attached thereto. The test specimen and material on the platen are in surface-to-surface contact with each other.

"Coefficient of friction" is defined as the measure of the relative difficulty when the surface of one material slides over an adjoining surface of either itself or of another material. "STATIC" coefficient of friction is described as the highest instantaneous value obtained to begin movement between the surfaces. "KINETIC" coefficient of friction is the average of the values obtained during the 60 seconds of the test (6 inch travel distance).

The sled used for the testing has a weight of 100 grams. Testing occurs in a room having a temperature of between about 22 degrees Celsius and about 24 degrees Celsius, and at a relatively humidity of about 50%.

The test table can be a moving platen known as the TMI Model 32-06, manufactured by Testing Machines, Inc. of Amityville, N.Y. The test platen is capable of a travel speed of 6 inches per minute.

The test material mounted to the platen preferably has a length of about 305 millimeters and a width of about 102–127 millimeters. The test material can be mounted to the platen (table) using a contact adhesive or double-sided tape.

The test material mounted to the sled preferably has a length of about 120 millimeters and a width of about 67 millimeters. The test material is mounted to the sled using a contact adhesive or double-sided tape.

The sled is positioned very lightly and gently on the surface of the moving platen to prevent any unnatural bond from developing. The length of the sled, the length of the connecting wire, and the length dimension of the plane-mounted material are parallel.

The moving platen is then put in motion at a velocity of 6 inches per minute. After movement of the platen removes slack from a connecting wire to a Chatillon DFI gate, the gage takes readings and continues to do so for about 60 seconds (6 inches of travel).

The gage measures and stores the "STATIC" value for the highest instantaneous coefficient of friction value obtained to begin the movement between the surfaces within the first inch of pull. The "KINETIC" value obtained and stored is the average of the values obtained during the 60 seconds of the test (6 inch travel distance).

The calculation for "KINETIC" coefficient of friction is obtained by the gage using the following equation. $\mu_k = A_K/B$, where $\mu_k$=the kinetic coefficient of friction value, $A_K$=the average gram value obtained during the 60 second test period, and B=sled weight of about 100 grams.

The calculation for "STATIC" coefficient of friction is obtained by the gage using the following equation. $\mu_s = A_s/B$, where $\mu_s$=the static coefficient of friction value, $A_s$=the maximum initial gram value obtained within the first inch of pull, and B=sled weight of about 100 grams.

TEST DATA/RESULTS

The following table shows test results including "STATIC" values and "KINETIC" values for the coefficient of friction for various test groups. The values listed in Table 1 are based on fifteen tests for Test Groups 1, 2, and 4, and the values listed for Test Group 3 are based on 5 tests.

Test Groups 1–4 all result from tests run on the stretch ears, outer cover, front outside surface of the diaper, back inside surface of the diaper, and the bodyside liner material of HUGGIES ULTRATRIM® Diaper made by Kimberly-Clark Corporation of Dallas, Tex., for the United States market in 1997.

Test Group 1 is defined as a test utilizing neck-bonded laminate material corresponding to the stretch ears of the above mentioned diaper mounted to the test sled. The material mounted to the table constitutes the front outside of the same diaper mentioned above. The HUGGIES ULTRATRIM® Diaper includes an intermittently attached loop patch or landing zone on the front outer cover of the diaper for securement to fastening tabs.

Test Group 2 includes elements from the same HUGGIES ULTRATRIM® diaper made by Kimberly-Clark Corporation. However, in Test Group 2, the table has the outer cover of the diaper mounted thereon, rather than the entire front portion of the diaper.

Test Group 3 includes the front outside of the same HUGGIES ULTRATRIM® Diaper as in Test Group 1, mounted on the moving plate (table). The sled receives the back inside surface of the same diaper. Thus during testing the back inside surface of the diaper is in surface-to-surface contact with the front outside surface.

Test Group 4 includes the bodyside liner of the same HUGGIES ULTRATRIM® Diaper described earlier, mounted to the sled. The outer cover mounted to the moving platen in Test Group 4 comprises the outer cover from a HUGGIES ULTRATRIM® Diaper as described earlier. During testing, the bodyside liner on the sled is in surface-to-surface contact with the outer cover.

TABLE 1

| SAMPLE ITEM | STATIC VALUE | STANDARD DEVIATION | KINETIC VALUE | STANDARD DEVIATION |
| --- | --- | --- | --- | --- |
| TEST GROUP 1 | 1.215 | 0.259 | 0.754 | 0.025 |
| TEST GROUP 2 | 0.689 | 0.053 | 0.614 | 0.044 |
| TEST GROUP 3 | 0.926 | 0.070 | 0.606 | 0.025 |
| TEST GROUP 4 | 0.458 | 0.049 | 0.401 | 0.019 |

The above tables show a "KINETIC" coefficient of friction value of much less than 1 for the various diaper elements tested. The "STATIC" values were higher for the tests of GROUP 1 and GROUP 3. However, these higher values occurred as the sled passed over an unattached loop patch edge on the diaper cover. The sled snagging or catching the diaper at the edge of the loop patch caused an increase in static coefficient of friction. Therefore, the static coefficient of friction values for Table Group 1 and Test Group 3 are not representative of the results where no landing zone or loop patch edge is present. In normal instances, for a diaper having no loop patch edge, the static coefficient of friction would have a lower value as seen in Test Groups 2 and 4 of Table 1.

Table 2 represents data collected from testing one embodiment of the invention. The test results include "STATIC" values and "KINETIC" values for the coefficient of friction for various test groups. The values listed in Table 2 are based on fifteen tests for Test Groups 5, 6, and 8, and the values listed for Test Group 7 are based on 5 attempted tests.

Test Groups 5–8 include Woodbridge polyurethane foam SM-64, made by Woodbridge Foam Fabricating, Inc. of Chattanooga, Tenn. The 2 millimeter thick foam material is mounted on the test sled. This foam material may be utilized as friction element 36 in fastening tab 30A of the illustrated embodiments of the invention. In Test Groups 5, 7 and 8, the polyurethane foam includes tab substrate 42 backing the foam material comprising spunbond-meltblown-spunbond material. The results between Test Groups 5 and 6 do not vary significantly. As expected, the presence or absence of tab substrate 42 has no significant effect on the coefficient of friction of the surface of friction element 36. This is so because the tab substrate 42 does not contact or act upon the outer cover material or the front portion of the diaper.

In Test Groups 5 and 6, the material mounted to the moving platen (table) is a neck bonded laminate. The neck bonded laminate is formed by two sheets of necked spunbond material secured in facing relationship to opposing sides of an elastomeric film core. The spunbond material comprises about 2 to about 2.5 denier polypropylene spunbond necked to reduce its width about 45% before being secured to the elastomeric film core. The spunbond material has a starting weight of 0.5 ounces per square yard. After necking, the spunbond material has a weight of about 0.65 to about 0.70 ounces per square yard. The neck bonded laminate comprises an extensible outer cover 22 for personal care article 8.

In Test Group 7 the outside front portion of a HUGGIES ULTRATRIM® Diaper, as mentioned in earlier tests, is mounted to the moving platen. In test Groups 7 and 8, polyurethane foam SM-64 is secured to the sled. In test Groups 8 the outer cover of a HUGGIES ULTRATRIM® Diaper is mounted to the moving platen (table).

TABLE 2

| SAMPLE ITEM | STATIC VALUE | STANDARD DEVIATION | KINETIC VALUE | STANDARD DEVIATION |
|---|---|---|---|---|
| TEST GROUP 5 | 8.027 | 1.191 | 5.690 | 0.666 |
| TEST GROUP 6 | 7.077 | 0.703 | 5.617 | 0.468 |
| TEST GROUP 7 | Greater than 15 | Unknown | Greater than 15 | Unknown |
| TEST GROUP 8 | 12.828 | 1.371 | 7.542 | 8.114 |

As clearly shown by the coefficient of friction values measured in Test Groups 5–8, the coefficient of friction for the Woodbridge polyurethane foam SM-64 is far greater than the coefficient of friction for the diaper of Test Groups 1–4.

No data was reported for Test Group 7. The reason no data was reported is because the coefficient of friction was so great (at least greater than 15), such that the test gage and sled could not measure the value. The coefficients of friction set forth in the above examples clearly prevent radial shifting of the fastening tab.

In view of the above information, the invention contemplates the use of friction elements 36 which have a coefficient of at least about 1.5, preferably at least about 3, more preferably at least about 5, and most preferably at least about 5.6.

Friction element 36 comprises a material having a coefficient of friction of at least about 1.5 when secured to a 100 gram sled and tested in contact with a neck bonded laminate material secured to a moving platen operating at a velocity of 6 inches per minute. The coefficient of friction preferably is greater than about 3, preferably greater than about 5, and most preferably greater than about 5.6 under the test conditions described above and described with respect to Table 2.

In embodiments where friction element 36 comprises a foam material, the foam material generally has an uncompressed thickness of less than about 10 millimeters, preferably less than about 5 millimeters, and most preferably less than about two millimeters.

Friction element 36 may have sufficient loft or resiliency such that a person perceives the element as having a cushion effect when contacting the skin of a wearer. Thus friction element 36 is configured to reduce irritation of the user's skin, even when in direct contact with the user's skin. Friction element 36 does not fasten or otherwise engage or bond outer cover 22 such as through use of adhesive, cohesive glues, and other natural and synthetic bonding agents. Friction element 36 assists in maintaining the original secured position of front portion 10 of personal care article 8 purely through surface-to-surface friction, or shear forces, when in contact with outer cover 22.

Importantly, friction element 36 has no adhesive tackiness and includes no securing elements providing a securement function for fastening tab 30A against front portion 10 of personal care article 8. Friction zone 34 contains no functional amount of tackifying agents. Thus friction element 36 provides no attachment of tabs 30A, 30B, to body substrate 20 when contacting front portion 10. However, the force of friction extant between the facing surfaces of friction element 36 and outer cover 22 maintains the relative positions of front portion 10 and fastening tab 30A, with respect to each other, when secured to the body of a user. Tackifying agents are disclosed in Ser. No. 777,997 filed Jan. 2, 1997 as a continuation of Ser. No. 576,418 filed Dec. 21, 1995, the disclosure of which is hereby incorporated by reference in a manner that is consistent (not contradictory) herewith.

As shown in FIG. 2, securing zone 32 may include a securing element 38. Securing element 38 may comprise hook components 40, such as known microhooks, of a hook and loop fastening system. Hook components 40 are employed to secure fastening tab 30A to front portion 10 of personal care article 8. Front portion 10 can include loop elements (not shown) mounted in landing zones for securement to hook components 40. Preferably, outer cover 22 comprises a material having looped construction such that hook components 40 secure directly to the outer cover. Such an arrangement reduces the number of elements that must be formed, placed, and secured to personal care article 8. Thus, such an arrangement reduces the cost of producing personal care article 8.

As shown in FIG. 2, tab substrate 42 underlies friction element 36 and securing element 38. Friction element 36 is mounted in surface-to-surface relationship with tab substrate 42 at friction zone 34. Likewise, securing element 38 is mounted in surface-to-surface relationship with tab substrate 42 in securing zone 32.

Securing element 38, may include flexible hook components 40, mounted in surface-to-surface relationship to tab substrate 42 using a layer 44 of adhesive as shown in FIG. 2. Layer 44 of adhesive is shown having a relatively large thickness for purposes of illustration. However, layer 44 can comprise a thin coating. Likewise, FIG. 2 shows layer 44 of adhesive permanently mounting friction element 36 to tab substrate 42. Other known methods of mounting securing element 38 and friction element 36 to tab substrate 42 may be utilized.

As shown in FIG. 2, securing element 38 fits the contour of tab substrate 42, especially at outside edge 46 of fastening tab 30A. Rectangular shaped friction element 36 also fits the shape of friction zone 34 where the friction element is mounted. Other shapes, of course, are contemplated for fastening tab 30A. The fastening tab shape shown in FIGS. 1 and 2 is merely for purposes of illustration, and other shapes are possible and intended.

Tab substrate 42 preferably comprises a non-woven material, such as spunbond-meltblown-spunbond material (SMS). Spunbond-meltblown-spunbond material comprises a layer of meltblown material located between and in surface-to-surface relationship with the spunbond layers. Such SMS material generally forms a fastening tab 30A that is substantially non-extensible during normal usage.

Other materials having suitable characteristics can be substituted for the above described tab substrates. For example, extensible materials can be utilized for tab substrate. Examples of extensible materials are described in U.S. Pat. No. 5,226,992 issued Jul. 13, 1993, to Morman, the disclosure of which is hereby incorporated by reference in a manner that is consistent (not contradictory) herewith.

While FIG. 2 illustrates securing element 38 being next to friction element 36 as being preferred, such an arrangement is not required. Fastening tab 30A can include an opening or space (not shown) along the length of, and between friction element 36 and securing element 38 for fastening tab 30A where tab substrate 42 comprises an exposed surface for a distance between the friction element and the securing element. Thus, in some embodiments, friction zone 34 and securing zone 32 can be spaced from one another, such that the edges thereof are not physically in contact with one another. An example of spaced elements for a fastening tab is shown in Ser. No. 421,640 filed Apr. 13, 1995 by Zehner et al, the disclosure of which is hereby incorporated by reference in its entirety, in a manner that is consistent (not contradictory) herewith.

While ultrasonic bonding is disclosed as the preferred method for mounting fastening tabs 30A, 30B to body substrate 20, other well known methods are contemplated. For example, curing adhesive, stitching, and pressure sensitive adhesives, are all potential mechanisms for suitably and permanently securing the inboard end of fastening tabs 30A, 30B to body substrate 20. As shown in FIG. 2, tab substrate 42 is secured to bodyside liner 24 of body substrate 20. Therefore, more of high coefficient of friction zone 34 can contact outer cover 22 and to a lesser extent, the body of a wearer. Other less preferred mounting locations, such as a location between outer cover 22 and bodyside liner 24 can be selected. However, less surface area of the high coefficient of friction zone 34 would be positioned to contact the body of a wearer.

After mounting fastening tabs 30A, 30B to body substrate 20, friction zones 34 extend inwardly of securing zones 32 on respective fastening tabs 30A, 30B. In this arrangement, friction zones 34 thus extend over part of bodyside liner 24 at opposing sides of rear portion 14 of personal care article 8.

Figure 4:
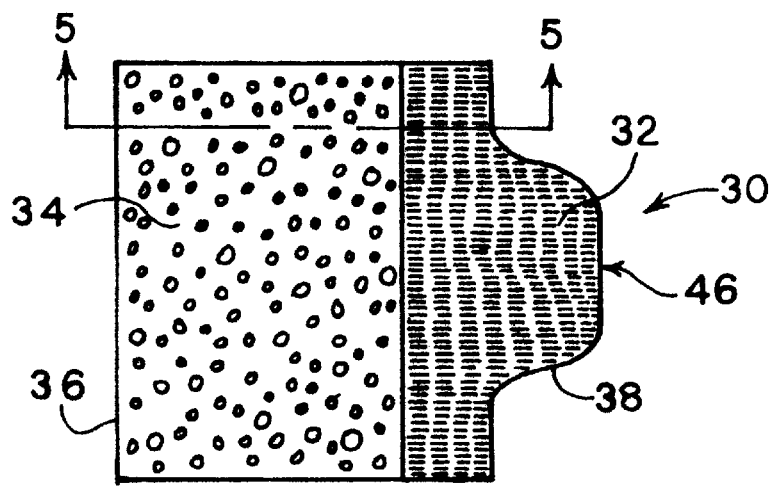
FIG. 4 shows a second embodiment of a tab for use with the personal care article of FIG. 1.
Figure 5:
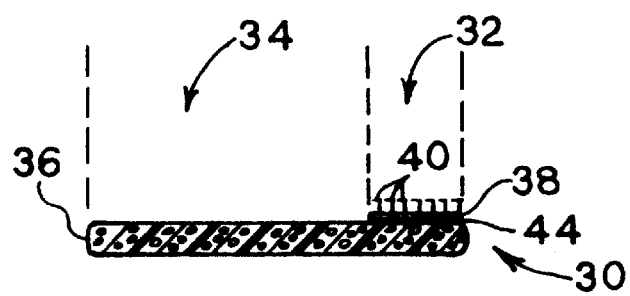
FIG. 5 shows a cross-section view of the tab of FIG. 4.

FIGS. 4 and 5 show another embodiment of the invention. In this embodiment, the thickness of friction element 36 can be greater than in the embodiment of FIGS. 1 and 2. Thickness of friction element 36 can be greater in the embodiment of FIG. 4 because the friction element provides the function performed by tab substrate 42 in the earlier embodiment of FIGS. 1 and 2. Securing element 38 is mounted in surface-to-surface relationship with a portion of friction element 36. Thus, the thickness of friction element 36 is not limited by being adjacent securing element 38.

In FIGS. 4 and 5, friction element 36 extends the entire length and width of fastening tab 30A. Thus, friction element 36 also functions as the underlying substrate for securing element 38. Friction zone 34 and securing zone 32 are located and function in a similar manner to the respective zones described in FIGS. 1 and 2.

As better shown in FIG. 5, securing element 38, including flexible hook components 40, is mounted at an end of friction element 36. Layer 44 of adhesive secures back side of securing element 38 to friction element 36 in surface-to-surface relationship therewith. As shown in FIG. 4, securing element 38 follows the contour of outside edge 46 of fastening tab 30A. In this manner, the embodiment of FIGS. 4 and 5 omits tab substrate 42. Thus the cost and number of steps needed to construct a fastening tab 30A, according to FIGS. 4 and 5, is reduced.

FIG. 5 shows securing element 38 extending to outside edge 46 of friction element 36. However, in other embodiments (not shown) securing element 38 can extend outwardly beyond outside edge 46 of fastening tab 30A. Thus, securing element 38 need not be supported over its entire length and width by an underlying element. Likewise, in the embodiment of FIG. 2, securing element 38 can extend outwardly beyond outside edge 46 of fastening tab 30A.

Other types of securing elements 38 besides flexible hook components 40 can be utilized to releasably secure fastening tab 30A to front portion 10 of personal care article 8. For example, securing element 38 can comprise a mechanical fastener, such as the loops, instead of the hooks of a hook and loop fastener system. An attachment surface (not shown) on outer cover 22 then comprises a corresponding hook material in front portion 10, adapted to releasably engage with the loop material of securing element 38 to hold and retain personal care article 8 on the body of the user.

Figure 7:
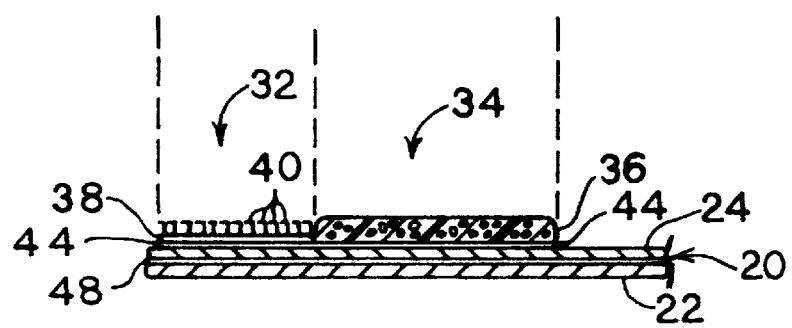
FIG. 7 shows a cross section of a first tab of the personal care article of FIG. 6.
Figure 6:
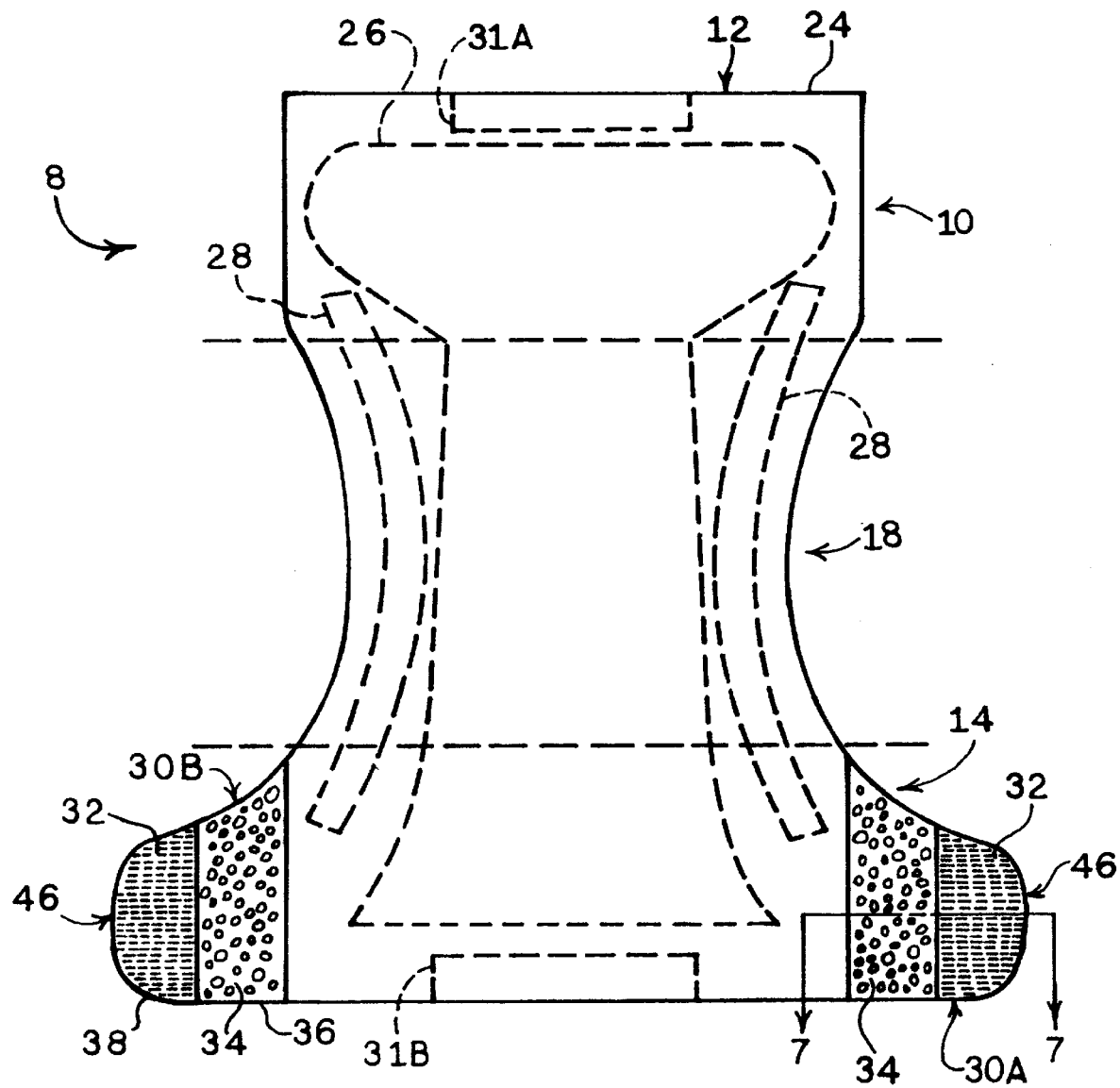
FIG. 6 shows a top view of a third embodiment of personal care articles of the invention.

FIGS. 6 and 7 show an embodiment of the invention having body substrate 20 formed by outer cover 22 and bodyside liner 24 acting as a tab substrate. Adhesive 48 secures outer cover 22 to bodyside liner 24. Therefore, in this embodiment no separate ear elements or ear materials are secured to personal care article 8.

As shown in FIG. 7, friction element 36 and securing element 38 are secured to, and substantially overlie in their entirety, body substrate 20. Adhesive 44 permanently secures friction element 36 and securing element 38 to bodyside liner 24. As shown in FIG. 6, securing zone 32 and friction zone 34 follow the contours of body substrate 20. Thus friction element 36 and securing element 38 do not have rectangular shapes in this embodiment.

The embodiment of FIG. 6 functions in a similar manner to the embodiment of FIG. 1. However, in FIGS. 6 and 7, a separate tab substrate 42 is not required because the body substrate 20 performs the function of the tab substrate. Thus the embodiment of FIG. 6 requires fewer elements to construct.

Figure 8:
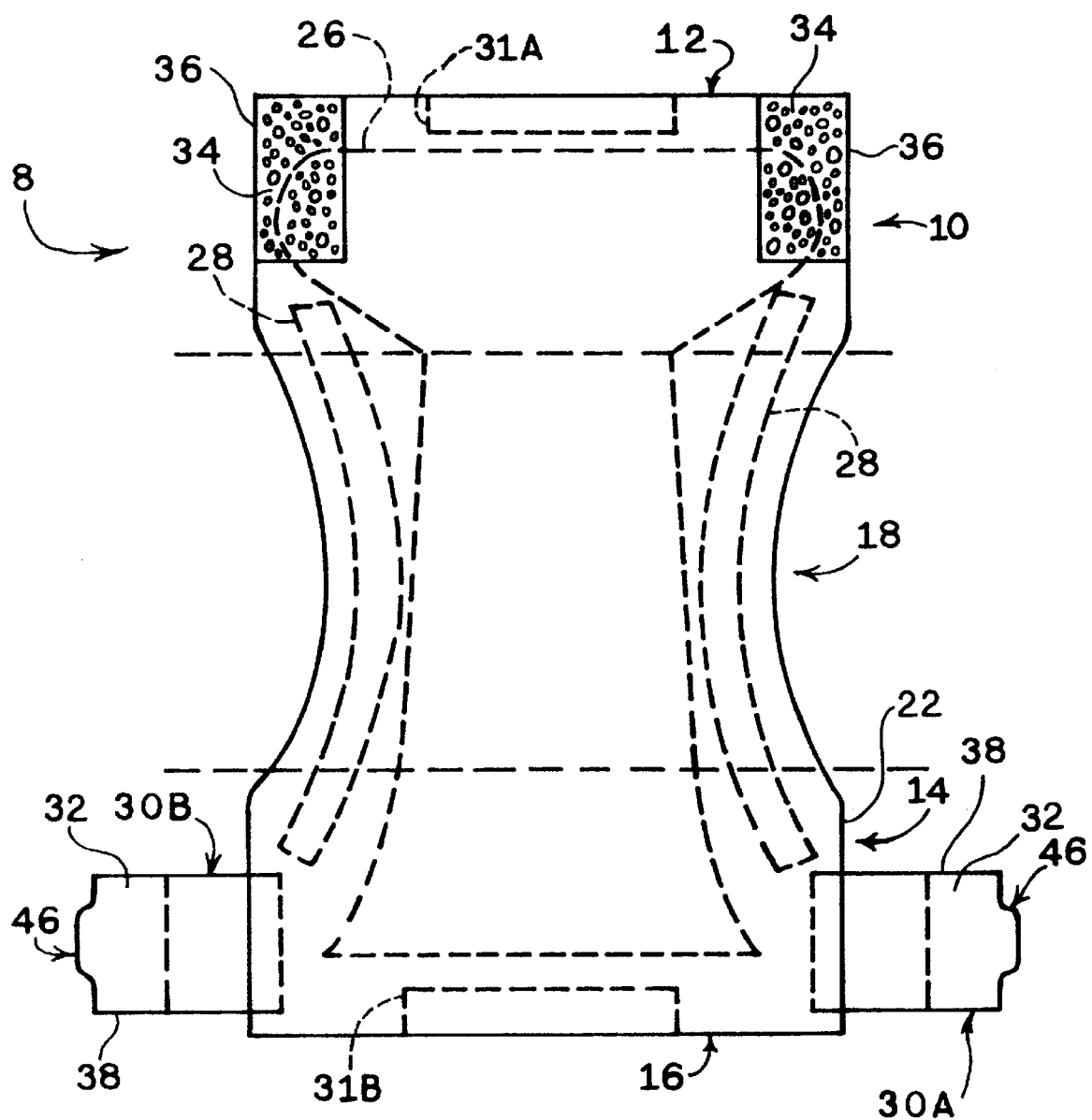
FIG. 8 shows a top view of a fourth embodiment of personal care articles of the invention.

FIG. 8 shows a top view of an outer cover side of another embodiment of personal care article 8. As in the embodiment of FIG. 1, personal care article 8 includes leg cuffs 28, waist elastics 31A, 31B, absorbent body 26, and fastening tabs 30A, 30B secured to rear portion 14 of the personal care article. Securing zones 32 and securing elements 38 are located at the outer ends of fastening tabs 30A, 30B. However, friction zones 34, including friction elements 36, are located at opposing ends of front portion 10 of personal care article 8. While FIG. 8 shows friction elements 36 that entirely overlie outer cover 22, the friction elements can also extend outwardly at opposing edges of front portion 10 or inwardly from the opposing edges.

The embodiment of FIG. 8 functions in a different way than the embodiment of FIG. 1. When fastening tabs 30A, 30B are secured to front portion 10, securing elements 38 are placed inwardly from friction elements 36. Friction elements 36 then are in surface-to-surface contact with respective portions of fastening tabs 30A, 30B inward from respective securing elements 38 and/or in contact with bodyside liner 24 of body substrate 20. Thus, even though friction elements 36 are not located on fastening tabs 30A, 30B, the result of use of the personal care article of FIG. 8 is similar to the results of FIG. 1.

In the embodiment of FIG. 8, friction elements 36 and securing elements 38 can comprise any of the elements disclosed herein. In addition, securing element 38 can comprise loops of a hook and loop fastening system, and hooks can be secured to outer cover 22 at front portion 10 of personal care article 8. Such an arrangement does not change the basic securement and radial shifting resistance functions of securing elements 38 and friction elements 36.

In a modification to the embodiment of FIG. 8, securing zones 32 can be secured to front portion 10 of personal care article 8. Securing zones 32 comprise securing elements 38 secured to front portion 10 inwardly from friction elements 36. This embodiment functions like the other embodiments, except, fastening tabs 30A, 30B include loop elements, for example, for securement to the securing elements 38 mounted to front portion 10 of personal care article 8.

In another embodiment (not shown), fastening tabs 30A, 30B can be permanently secured to opposing sides of front portion 10 of personal care article 8. In such instances, fastening tabs 30A, 30B are then selectively secured to rear portion 14 of personal care article 8. Thus, the fastening tabs are entirely reversed with respect to the embodiment shown in FIG. 1.

Other well known fastening apparatus can instead be used to support personal care article 8 on the user. For example, a cohesive system, an adhesive fastener system, mechanical system, or the like may be utilized as securing elements 38, with suitable cooperating elements or front portion 10, as necessary, to support personal care article 8 on the user.

In operation, personal care article 8 of FIG. 1 is secured to outer cover 22 at front portion 10 using first fastening tab 30A, and second opposing fastening tab 30B. Second fastening tab 30B has elements of same character as first fastening tab 30A shown in FIG. 2. Thus second fastening tab 30B has a third side, a third surface on the third side having a second friction zone 34, and a second securing zone 32 on the third side adjacent the friction zone 34. In use, first and second securing zones 32, located at outboard ends of tabs 30A, 30B are secured to outer cover 22 in front portion 10. The respective friction zones 34 are located inwardly from the respective outboard edges 46 of fastening tabs 30A, 30B, and thus generally inwardly of securing zones 32.

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, all such arrangements, modifications, and alterations are intended to be within the scope of the appended claims.

To the extent the following claims use means plus function language, it is not meant to include there, or in the instant specification, anything not structurally equivalent to what is shown in the embodiments disclosed in the specification.

What is claimed is:

1. A personal care article for being worn on a body of a wearer, wherein said personal care article having a rear portion, a front portion, and a crotch portion, said personal care article comprising:

a body substrate including an outer cover and a bodyside liner, wherein said bodyside liner is in facing relationship to said outer cover;

first and second fastening tabs each being secured to and extending outwardly from said body substrate at opposing sides of said rear portion of said personal care article, each of said first and second fastening tabs including a tab substrate, a securing zone having a securing element, and a friction zone having a friction element, each of said tab substrates supporting said securing element and said friction element and being made of a substantially non-extensible material without any one of pleats, gathers, and other means for extension of said tab substrates, said securing zones being located proximate outer ends of each of said first and second fastening tabs, said friction zone being located inwardly of each of said securing zones, said friction zones providing no securement of said first and second fastening tabs to said personal care article, said securing zones of said first and second fastening tabs securing said first and second fastening tabs to said outer cover at said front portion of said personal care article, and said friction zones stabilizing said front portion with respect to said rear portion by resisting relative surface-to-surface movement of said front portion relative to said first and second fastening tabs.

2. The personal care article as in claim 1, further comprising an absorbent body located between said bodyside liner and said outer cover, wherein said personal care article is an absorbent article for receiving exudates exuded from the body of the wearer of said personal care article.

3. The personal care article as in claim 1, wherein said friction zones prevent opposing sides of said front portion and each of said first and second fastening tabs from surface-to-surface radial shifting relative to each other in response to body forces exerted thereon by the wearer of said personal care article.

4. The personal care article as in claim 1, wherein said friction elements are comprised of materials having sufficient softness to prevent leaving red marks on a leg of the wearer of said personal care article at leg openings closed by said first and second fastening tabs.

5. The personal care article as in claim 4, wherein said materials having an uncompressed thickness of less than about 5 millimeters.

6. The personal care article as in claim 1, wherein said friction elements are coextruded films, said coextruded films comprising polyethylene and polyolefin, and said coextruded films having sufficient softness to prevent leaving red marks on a leg of the wearer of said personal care article at leg openings closed by said first and second fastening tabs.

7. The personal care article as in claim 1, wherein said friction elements are comprised of coatings formed from at least one of a group of materials consisting of: ethylene vinyl acetate copolymers applied as any one of a hot melt and as a water-based coating having at least 28% vinyl acetate; polyvinyl acetate in water-based emulsions; styrene-butadiene any one of in an emulsion and as a hot melt; cellulose acetate butyrate in a hot melt; ethyl cellulose blended with a plasticizer and a resin; unblended acrylics in an emulsion system; synthetic rubber; rubber; resin; plasticizer blends; and hot melts including polyethylene and polyamides.

8. The personal care article as in claim 1, wherein said securing elements are comprised of microhooks for securement to said outer cover in said front portion of said personal care article.

9. The personal care article as in claim 1, wherein portions of said friction elements support said securing elements.

10. The personal care article as in claim 1, wherein said outer cover comprises a material extensible in at least one direction.

11. The personal care article as in claim 1, wherein said bodyside liner comprises a material extensible in at least one direction.

12. The personal care article as in claim 1, wherein said first and second fastening tabs are secured to said bodyside liner at opposing sides of said rear portion of said personal care article by ultrasonic bonding.

13. The personal care article as in claim 1, wherein said friction zones are free from functional amounts of tackifying agents.

14. The personal care article as in claim 1, wherein said friction zones extend inwardly on said first and second fastening tabs such that said friction zones extend over part of said body substrate at opposing sides of said rear portion of said personal care article.

15. The personal care article for being worn on a body of a wearer, wherein said personal care article has a rear portion, a front portion, and a crotch portion, said personal care article comprising:

a body substrate including an outer cover and a bodyside liner, wherein said bodyside liner is in facing relationship to said outer cover;

first and second fastening tabs each including a tab substrate made of a substantially non-extensible material without any one of pleats, gathers, and other similar means for extension of said tab substrate, each of said first and second fastening tabs being secured to said body substrate at opposing sides of said rear portion of said personal care article, and each of said first and second fastening tabs including a securing zone located proximate an outer end of each of said first and second fastening tabs; and friction zones located on an outer surface of said front portion of said personal care article at opposing sides thereof, each of said friction zones being comprised of a friction element, said friction elements providing no securement of said front portion to any one of said first and second fastening tabs and said rear portion, said securing zones of said first and second fastening tabs securing said first and second fastening tabs to said outer cover at said front portion of said personal care article, said securing zones being placed inwardly from said friction elements when secured to said outer surface of said front portion of said personal care article worn on the body of the wearer thereof, said friction elements stabilizing said front portion with respect to said rear portion of said personal care article, and resisting relative surface-to-surface movement of said first and second fastening tabs with respect to said friction elements.

16. The personal care article as in claim 15, wherein said first and second fastening tabs extend outwardly from said body substrate at opposing sides of said rear portion of said personal care article.

17. A personal care article for being worn on a body of a wearer, wherein said personal care article has a rear portion, a front portion, and a crotch portion, said personal care article comprising:

a body substrate including an outer cover and a bodyside liner, wherein said bodyside liner is in facing relationship to said outer cover; and first and second fastening tabs each being secured to and extending outwardly from said body substrate at opposing sides of said rear portion said personal care article, each of said first and second fastening tabs including a tab substrate, a securing zone having a securing element, and a friction zone comprised of a friction element, each of said tab substrate supporting said securing element and said friction element and being made of a substantially non-extensible material without any one of pleats, gathers, and other means for extension thereof, said friction elements providing substantially no securement of said first and second fastening tabs to said personal care article, said friction elements having a kinetic coefficient of friction of at least about 1.5 when measured against said outer cover.

18. The personal care article as in claim 17, wherein said securing zones secure said first and second fastening tabs to said outer cover at said front portion of said personal care article, and said friction elements stabilize said front portion with respect to said rear portion by resisting relative surface-to-surface movement of said front portion with respect to said first and second fastening tabs.

19. The personal care article as in claim 18, wherein said securing zones are located proximate outer ends of said first and second fastening tabs.

20. The personal care article as in claim 18, wherein said securing elements are in surface-to-surface relationship with said tab substrates at said securing zones.

21. The personal care article as in claim 18, wherein said outer cover is comprised of a polyproplyene necked spunbonded laminate.

22. The personal care article as in claim 21, wherein said friction elements are comprised of a foam material.

23. The personal care article as in claim 22, wherein said kinetic coefficient of friction of said foam material of said friction elements is at least about 3 when measured against said polypropylene necked spunbonded laminate of said outer cover.

24. The personal care article as in claim 17, wherein said kinetic coefficient of friction of said friction elements is at least about 5.0 when measured against said outer cover.

25. A personal care article for being worn on a body of a wearer, wherein said personal care article has a rear portion, a front portion, and a crotch portion, said personal care article comprising:

a body substrate including an outer cover and a bodyside liner, wherein said bodyside liner is in facing relationship to said outer cover; and first and second fastening tabs each secured to and extending outwardly from said body substrate at opposing sides of said rear portion of said personal care article, each of said first and second fastening tabs including a tab substrate, a securing zone, and a fastening zone, said tab substrates being made of a substantially non-extensible material without any one of pleats, gathers, and other similar means for extension of said tab substrate, said securing zones located proximate outer ends of said first and second fastening tabs said friction zones located inwardly of said securing zones, said friction zones providing no securement of said first and second fastening tabs to said personal care article, said securing zones of said first and second fastening tabs securing said first and second fastening tabs to said outer cover at said front portion of said personal care article, and said friction zones stabilizing said front portion with respect to said rear portion by resisting relative surface-to-surface movement to said front portion relative to said first and second fastening tabs.

26. The personal care article as in claim 25, further comprising an absorbent body located between said bodyside liner and said outer cover so that said personal care article forms an absorbent article for receiving exudates exuded from the body of the wearer of the absorbent article.

27. The personal care article as in claim 25, wherein said friction zones prevent opposing sides of said front portion and said first and second fastening tabs from surface-to-surface radial shifting relative to each other in response to body forces exerted by the wearer of said personal care article.

28. The personal care article as in claim 25, wherein said friction zones are comprised of friction elements.

29. The personal care article as in claim 28, wherein said friction zones are comprised of materials having sufficient softness to prevent leaving red marks on a leg of the wearer of said absorbent care article at leg openings closed by said first and second fastening tabs.

30. The personal care article as in claim 29, wherein said materials of said friction elements have uncompressed thickness of less than about 5 millimeters.

31. The personal care article as in claim 28, wherein said friction elements are comprised of coextruded films, said coextruded films comprising polyethylene and polyolefin, and said coextruded films have a sufficient softness to prevent leaving red marks on a leg of the wearer of said absorbent care article at leg openings closed by said first and second fastening tabs.

32. The personal care article as in claim 28, wherein said friction elements are comprised of coatings formed from at least one of a group consisting of: ethylene vinyl acetate copolymers applied as any one of a hot melt and as a water based coating having at least 28% vinyl acetate; polyvinyl acetate in water-based emulsions; styrene-butadiene any one of in an emulsion and as a hot melt; cellulose acetate butyrate in a hot melt; ethyl cellulose blended with a plasticizer and a resin; unblended acrylics in an emulsion system; synthetic rubber; rubber; resin; plasticizer blends; and hot melts including polyethylene and polyamides.

33. The personal care article as in claim 25, wherein said securing zones are comprised of securing elements.

34. The personal care article as in claim 33, wherein said securing elements are comprised of microhooks for securement to said outer cover in said front portion of said personal care article.

35. The personal care article as in claim 34, wherein said friction zones are comprised of friction elements.

36. The personal care article as in claim 35, wherein said tab substrates supporting said securing elements and said friction elements.

37. The personal care article as in claim 35, wherein portions of said friction elements support said securing elements.

38. The personal care article as in claim 25, wherein said outer cover is comprised of a material extensible in at least one direction.

39. The personal care article as in claim 25, wherein said bodyside liner is comprised of a material extensible in at least one direction.

40. The personal care article as in claim 25, wherein said first and second fastening tabs are secured to said bodyside liner at opposing sides of said rear portion of said personal care article by ultrasonic bonding.

41. The personal care article as in claim 25, wherein said friction zones are free from functional amounts of tackifying agents.

42. The personal care article as in claim 25, wherein said friction zones extend inwardly on said first and second fastening tabs such that said friction zones extend over part of said body substrate at opposing sides of said rear portion of said personal care article.

43. A personal care article for being worn on a body of a wearer, wherein said personal care article has a rear portion, a front portion, and a crotch portion, said personal care article comprising:

a body substrate including an outer cover and a bodyside liner, wherein said bodyside liner is in facing relationship to said outer cover; and first and second fastening tabs each including a tab substrate being made of a substantially non-extensible material without any one of pleats, gathers, and other means for extension of said tab substrates, each of said first and second fastening tabs being secured to and extending outwardly from said body substrate at opposing sides of said rear portion of said personal care article, each of said first and second fastening tabs including a friction zone and being comprised of a friction element, said friction elements providing substantially no securement of said first and second fastening tabs to said personal care article, and said friction elements having a kinetic coefficient of friction of at least about 1.5 when measured against said outer cover.

44. The personal care article as in claim 43, wherein each of said first and second fastening tabs include a securing zone, said securing zones securing said first and second fastening tabs to said outer cover at said front portion of said personal care article and each of said friction zones including said friction element for stabilizing said front portion with respect to said rear portion by resisting relative surface-to-surface movement of said front portion with respect to said first and second fastening tabs.

45. The personal care article as in claim 44, wherein said securing zones are located proximate outer ends of said first and second fastening tabs.

46. The personal care article as in claim 44, wherein said securing zones include securing elements, and said first and second fastening tabs include tab substrates supporting both said securing elements and said friction elements.

47. The personal care article as in claim 46, wherein said securing elements are in surface-to-surface relationship with said tab substrate at said securing zones.

48. The personal care article as in claim 44, wherein said outer cover is comprised of a polypropylene necked spunbond laminate.

49. The personal care article as in claim 48, wherein said friction element is comprised of a foam material.

50. The personal care article as in claim 49, wherein said kinetic coefficient of friction of said foam material of said friction elements is at least about 3 when measured against said polypropylene necked spunbond of said outer cover.

51. The personal care article as in claim 43, wherein said kinetic coefficient of friction of said friction element is at least about 5.0 when measured against said outer cover.

52. The personal care article as in claim 15, wherein said friction elements have a kinetic coefficient of friction of at least about 3 when measured against a friction of a polypropylene necked spunbonded laminate, said spunbonded laminate being comprised of first and second polypropylene spunbonded layers having a weight of about 0.65 to 0.70 ounces per square yard after necking, and a fiber size of about 2 to about 2.5 denier, said necked spunbonded laminate including an elastomeric film core in surface-to-surface relationship with said spunbonded layers, said kinetic coefficient of friction of said friction elements measured at a temperature of between about 22 degrees and about 24 degrees Celsius, when said friction zones are secured to about 100 gram sled and said polypropylene necked spunbonded laminate is secured to a moving platen.

* * * * *

UNITED STATES PATENT AND TRADEMARK OFFICE
CERTIFICATE OF CORRECTION

PATENT NO.   : 6,099,516
DATED        : August 8, 2000
INVENTOR(S)  : Jennifer E. Pozniak, et al.

Page 1 of 1

It is certified that error appears in the above-identified patent and that said Letters Patent is hereby corrected as shown below:

Column 5,
Line 8, delete "2" and insert "22" in place thereof.

Column 6,
Line 5, delete "cove" and insert "cover" after the first occurrence of the word "outer".

Claim 15,
Line 1, delete "The and insert -- A -- in place thereof.

Claim 29,
Line 2, delete "zones" and insert -- elements -- in place thereof.

Claim 52,
Line 6, after "to" insert -- about --.

Signed and Sealed this

Twentieth Day of November, 2001

Attest:

*Attesting Officer*

NICHOLAS P. GODICI
*Acting Director of the United States Patent and Trademark Office*